(12) United States Patent
Palomar-Moreno et al.

(10) Patent No.: US 10,881,619 B2
(45) Date of Patent: Jan. 5, 2021

(54) COMPOSITIONS, DEVICES AND METHODS FOR MULTI-STAGE RELEASE OF CHEMOTHERAPEUTICS

(71) Applicant: Boston Scientific Scimed, Inc., Maple Grove, MN (US)

(72) Inventors: Javier Palomar-Moreno, Galway (IE); Michelle Hannon, Galway (IE); Phillip Bannister, Longford (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 576 days.

(21) Appl. No.: 14/980,371

(22) Filed: Dec. 28, 2015

(65) Prior Publication Data

US 2016/0184233 A1 Jun. 30, 2016

Related U.S. Application Data

(60) Provisional application No. 62/097,410, filed on Dec. 29, 2014.

(51) Int. Cl.
*A61K 9/50* (2006.01)
*A61M 25/10* (2013.01)
(Continued)

(52) U.S. Cl.
CPC .......... *A61K 9/5078* (2013.01); *A61K 9/0024* (2013.01); *A61L 29/16* (2013.01);
(Continued)

(58) Field of Classification Search
None
See application file for complete search history.

(56) References Cited

U.S. PATENT DOCUMENTS 9,764,065 B2 9/2017 Wang
2004/0117005 A1 6/2004 Nagarada Gadde et al.
(Continued)

FOREIGN PATENT DOCUMENTS

CN 103040757 A 4/2013
CN 103735516 A 4/2014
(Continued)

OTHER PUBLICATIONS

International Search Report and Written Opinion dated Mar. 24, 2016 for International Application No. PCT/US2015/067637 (11 pages).
(Continued)

*Primary Examiner* — Dominic Lazaro
(74) *Attorney, Agent, or Firm* — Kacvinsky Daisak Bluni PLLC

(57) ABSTRACT

In one aspect, the present disclosure provides microparticles that are configured to release a first drug over a first time period and to release a second drug over a second time period, wherein a lag period of substantially no drug release occurs between the first and second time periods. In other aspects, the present disclosure pertains to the use of such microparticles in delivery systems and methods of treatment. In another aspect, the present disclosure pertains to drug delivery systems that comprising a folded inflatable drug delivery balloon that comprises folds and microparticles positioned within the folds.

33 Claims, 2 Drawing Sheets

(51) Int. Cl.
*A61L 31/08* (2006.01)
*A61L 31/16* (2006.01)
*A61L 31/14* (2006.01)
*A61K 9/00* (2006.01)
*A61L 29/16* (2006.01)

(52) U.S. Cl.
CPC .... *A61M 25/1002* (2013.01); *A61L 2300/416* (2013.01); *A61M 2025/1004* (2013.01); *A61M 2025/105* (2013.01)

(56) References Cited

U.S. PATENT DOCUMENTS

| | | | |
|---|---|---|---|
| 2005/0064005 A1* | 3/2005 | Dinh | A61L 27/34 424/422 |
| 2006/0228453 A1 | 10/2006 | Cromack et al. | |
| 2007/0185569 A1* | 8/2007 | Hahn | A61F 2/82 623/1.46 |
| 2008/0281409 A1 | 11/2008 | Malone et al. | |
| 2011/0099789 A1* | 5/2011 | Ewing | A61M 25/1002 29/428 |
| 2011/0264188 A1* | 10/2011 | Doshi | A61L 29/16 623/1.11 |
| 2012/0013043 A1 | 1/2012 | Weber et al. | |
| 2013/0323312 A1* | 12/2013 | Blaskovich | A61K 9/4866 424/497 |
| 2014/0199381 A1 | 7/2014 | Ying et al. | |

FOREIGN PATENT DOCUMENTS

| | | |
|---|---|---|
| JP | 2003212756 | 7/2003 |
| JP | 2003212756 A | 7/2003 |
| JP | 2006213600 A | 8/2006 |
| JP | 2007502281 A | 2/2007 |
| JP | 2007215620 A | 8/2007 |
| JP | 2007535418 A | 12/2007 |
| JP | 2009530039 A | 8/2009 |
| JP | 2010508901 A | 3/2010 |
| JP | 2010540159 A | 12/2010 |
| JP | 2014083109 A | 5/2014 |
| WO | 0247581 A1 | 6/2002 |
| WO | 2002047581 A1 | 6/2002 |
| WO | 2011024831 A1 | 3/2011 |

OTHER PUBLICATIONS

K. Milewski, "Intra-Arterial Application of Biodegradable Nanoparticles Loaded with Everolimus", (May 20-23, 2014).
Roy et al., "Multiparticulate formulation approach to pulsatile drug delivery: Current perspectives", Journal of Controlled Release, 2009, vol. 134, No. 2, pp. 74-80.
Urata, T. et al., "Modification of release rates of cyclosporin a from polyl(L-lactic acid) microspheres by fatty acid esters and in-vivo evaluation of the microspheres" Journal of Controlled Release, May 1999, vol. 58, Issue 2, pp. 133-141.
Zhu, Weiwei et al., "Development of a Sustained-Release System for Perivascular Delivery of Dipyridamole" Journal of Biomedical Materials Research Part B Applied Biomaterials, Apr. 2006, vol. 77B, Issue 1, pp. 135-143.

* cited by examiner

COMPOSITIONS, DEVICES AND METHODS FOR MULTI-STAGE RELEASE OF CHEMOTHERAPEUTICS

STATEMENT OF RELATED APPLICATION

This application claims the benefit of U.S. Application No. 62/097,410 filed on Dec. 29, 2014 and entitled "COMPOSITIONS, DEVICES AND METHODS FOR MULTI-STAGE RELEASE OF CHEMOTHERAPEUTICS," which is hereby incorporated by reference in its entirety.

FIELD OF THE APPLICATION

This application relates to the field of medical devices. More particularly, the application is related to the delivery of drugs to the vasculature.

BACKGROUND

Embolization is a minimally invasive procedure that makes use of particles to selectively block the blood supply to unwanted biological tissues such as tumors, leading to tissue death. Various polymer-based particles, typically microspheres, are currently employed for embolization procedures. These microspheres are usually introduced to the location of the intended embolization through microcatheters. In a typical embolization procedure, local anesthesia is first given over a common blood vessel. The blood vessel is then percutaneously punctured and a catheter is inserted and fluoroscopically guided into the area of interest. An angiogram may then be performed by injecting contrast agent through the catheter. An embolic agent is then deposited through the catheter. A follow-up angiogram is usually performed to determine the specificity and completeness of the arterial occlusion.

Various commercially available embolic microspheres are composed of polymers. Materials commonly used commercially for this purpose include polyvinyl alcohol (PVA), acetalized PVA (e.g., Contour SE™ embolic agent, Boston Scientific, Natick, Mass., USA) and crosslinked acrylic hydrogels (e.g., Embospheres®, Biosphere Medical, Rockland, Mass., USA). Similar microspheres have been used in transarterial chemoembolization (TACE) to increase the residence time of the chemotherapy agent after delivery. In one specific instance, a chemotherapy agent (doxorubicin) has been directly added to polyvinyl alcohol hydrogel microspheres such that it can be released locally after delivery (e.g., DC Bead™ drug delivery chemoembolization system, Biocompatibles International plc, Farnham, Surrey, UK).

The present disclosure pertains to methods, compositions and devices which provide multi-stage drug release and which present an alternative to traditional transarterial chemoembolization procedures.

SUMMARY

In one aspect, the present disclosure provides delivery systems for delivering a one or more drugs to a subject, the delivery systems comprising: (a) a delivery device configured to release microparticles into a feeder artery within a body of a subject and (b) microparticles that are configured to release a first drug over a first time period and to release a second drug over a second time period, wherein a lag period of substantially no drug release occurs between the first and second time periods, and wherein the first drug and the second drug may be the same or different.

In another aspect, the present disclosure provides methods of treatment that comprise delivering therapeutic-agent releasing microparticles into a feeder artery of a tumor, wherein the microparticles release a first drug over a first time period, wherein the microparticles release a second drug over a second time period, wherein a lag period of substantially no drug release occurs between the first and second time periods, and wherein the first drug and the second drug may be the same or different. In certain embodiments, the microparticles may be delivered using delivery systems such as those described in the prior paragraph.

In certain embodiments, which may be used in combination with any of the above aspects and embodiments, the first and second drugs may be anti-cancer drugs.

In certain embodiments, which may be used in combination with any of the above aspects and embodiments, the lag period may range from 2 to 6 weeks.

In certain embodiments, which may be used in combination with any of the above aspects and embodiments, the first time period may be a period of five days or less and the second time may be a period of five days or less.

In certain embodiments, which may be used in combination with any of the above aspects and embodiments, 30 to 70% of the total cumulative drug release from the microparticles occurs over the first time period, 30 to 70% of the total cumulative drug release from the microparticles occurs over the second time period, and/or less than 5%, more beneficially less than 1%, of the total cumulative drug release occurs over the lag period.

In certain embodiments, which may be used in combination with any of the above aspects and embodiments, the microparticles may comprise: (a) a bioerodible core that comprises the second drug, (b) a first bioerodible layer surrounding the bioerodible core that comprises substantially no drug, and (c) a second bioerodible layer surrounding the first bioerodible layer that comprises the first drug.

In certain embodiments, which may be used in combination with any of the above aspects and embodiments, the microparticles may comprise: (a) first microparticles that comprise the first drug but not the second drug and release the first drug over the first time period and (b) second microparticles that comprise the second drug but not the first drug and release the second drug over the second time period.

In certain embodiments, which may be used in combination with any of the above aspects and embodiments, the delivery device may comprises a balloon in which cases the microparticles may be beneficially provided on a surface of the balloon, in some instances, positioned within the folds of the balloon, for example, such that the microparticles are released from the folds upon inflation of the balloon. The balloon may be adapted, for example, to be inflated in a feeder artery of a tumor (e.g., in a hepatic artery, renal artery, etc.) and deliver the microparticles to the feeder artery.

In other aspects, which may be used in combination with any of the above aspects and embodiments, a drug delivery system is provided, which comprises a folded inflatable drug delivery balloon that comprises folds and microparticles positioned within the folds, wherein the microparticles are printed on a surface of the balloon before forming the folds (e.g., by a ink jet printing process, a three-dimensional printing process, etc.) or wherein the microparticles are injected into the folds after forming the folds.

Advantages of the present disclosure include the ability to reduce the number of therapeutic interventions required (thereby minimizing the stress of repeated interventional procedures) by providing microparticles, devices, systems and methods that allow for a controlled release of a first drug, followed by a lag period of substantially no drug release (e.g., to allow a patient rest between repeated chemotherapy sessions), followed by release of a second drug, which may be the same or different than the first drug.

These and other aspects, embodiments, and advantages will become clear to those of ordinary skill in the art upon review of the detailed description to follow.

BRIEF DESCRIPTION OF THE DRAWINGS

Aspects of the disclosure are described below with reference to the following drawings in which like numerals reference like elements, and wherein.

Figure 1:
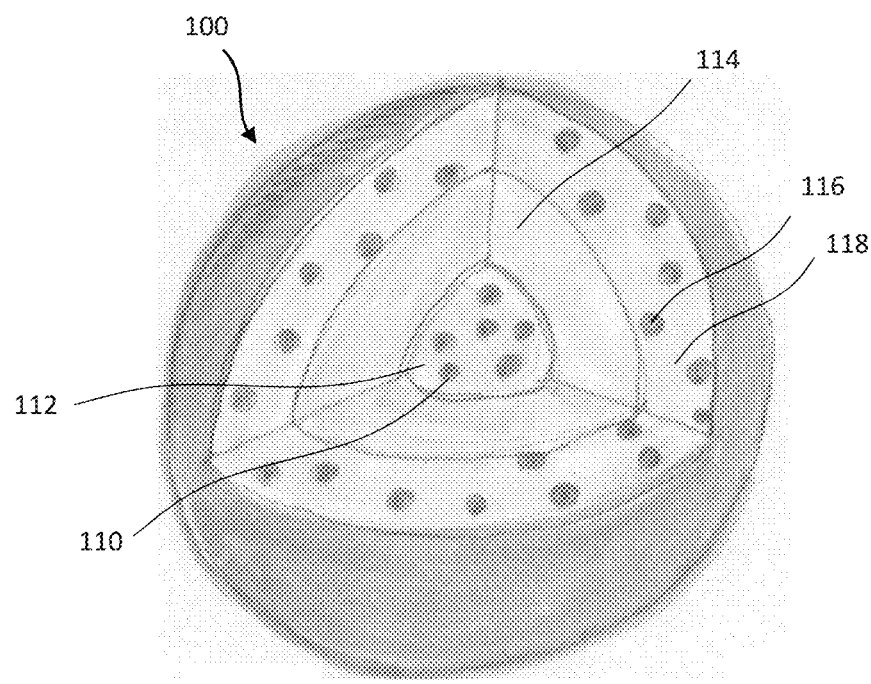
FIG. 1 is a schematic cut-away view of a multi-stage release microparticle.

Unless otherwise provided in the following specification, the drawings are not necessarily to scale, with emphasis being placed on illustration of the principles of the disclosure.

DETAILED DESCRIPTION OF THE PREFERRED EMBODIMENTS

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

In various aspects, the present disclosure pertains to methods of treatment of structures and organs, including treatment of solid tumors such as those associated with cancers such as liver cancer, renal carcinoma and bone tumors, among various others, as well as treatment of benign tumors such as uterine fibroids. In these methods, drug releasing microparticles are introduced into a feeder artery for the structure or organ. Once delivered, the microparticles release a first drug over a first time period and subsequently release a second drug over a second time period. In various embodiments, there is a lag period between the first time period and the second time period, which may also be referred to herein as a lag period, over which substantially no drug release occurs.

Depending on the embodiment, the first drug and the second drug may be the same or different. In various embodiments, the first and second drugs are anti-cancer agents.

Examples of anti-cancer agents include (a) cytotoxic antibiotics including anthracyclines, such as doxorubicin, daunorubicin, epirubicin, idarubicin, pirarubicin, aclarubicin and mitoxantrone, as well as actinomycin, bleomycin, plicamycin, mitomycin, (b) alkylating agents, including nitrogen mustards (e.g. mechlorethamine, cyclophosphamide, melphalan, chlorambucil, ifosfamide, busulfan, etc.), nitrosoureas (e.g., N-Nitroso-N-methylurea, carmustine, lomustinem, semustine, fotemustine, streptozotocin, etc.), tetrazines (e.g., dacarbazine, mitozolomide, temozolomide, etc.), aziridines (e.g., thiotepa, mytomycin, diaziquone, etc.), cisplatins and derivatives (e.g., include cisplatin, carboplatin, oxaliplatin, etc.), and non-classical alkylating agents (e.g., procarbazine and hexamethylmelamine, etc.), (c) anti-metabolites including anti-folates (e.g., methotrexate, pemetrexed, etc.), fluoropyrimidines (e.g., 5-fluorouracil, capecitabine, etc.), deoxynucleoside analogs (e.g., cytarabine, gemcitabine, decitabine, vidaza, fludarabine, nelarabine, cladribine, clofarabine, pentostatin, etc.) and thiopurines (e.g., thioguanine, mercaptopurine, etc.), (d) topoisomerase inhibitors including topoisomerase I inhibitors (e.g., irinotecan, topotecan, camptothecin etc.) and topoisomerase II inhibitors (e.g., etoposide, doxorubicin, mitoxantrone, teniposide, novobiocin, merbarone, aclarubicin, etc.), and (e) anti-microtubule agents including vinca alkaloids (e.g., vincristine, vinblastine, vinorelbine, vindesine, vinflunine, etc.) and taxanes (e.g., paclitaxel, docetaxel, etc.), podophyllotoxin, etoposide and teniposide.

Particularly beneficial agents include doxorubicin, cisplatin, fluorouracil (e.g., 5-fluorouracil), and gemcitabine.

The first time period, second time period and lag period may vary significantly from embodiment to embodiment. In some embodiments, the first time period over which the first drug is released is 5 days or less. In some embodiments, the second time period over which the second drug is released is 5 days or less. In some embodiments, the lag period between the first time period and the second time period ranges from 2 weeks to 6 weeks, more typically from 3 weeks to 5 weeks, even more typically about 4 weeks.

In certain embodiments, between 30 wt % and 70 wt % of the total cumulative release of the drug from the microparticles (i.e., the total release over the lifetime of the microparticles), preferably between 40 wt % and 60 wt %, may occur over the first time period, and between 70 wt % and 30 wt % of the total cumulative release of the drug from the microparticles, preferably between 60 wt % and 40 wt %, may occur over the second time period. Preferably, less than 5 wt %, more preferably less than 1 wt %, of the total cumulative release of the drug from the microparticles may occur over the lag period. In some embodiments, particles may be created in which the first and second drugs are released in substantially different doses.

In certain embodiments, the microparticles range in width (e.g., the diameter of a spherical microparticle, the diameter of a cylindrical microparticle, etc.) from 1 nm to 500 μm or more, for example, ranging in width from 1 nm to 2.5 nm to 5 nm to 10 nm to 25 nm to 50 nm to 100 nm to 250 nm to 500 nm to 1 μm to 2.5 μm to 5 μm to 10 μm to 25 μm to 50 μm to 100 μm to 150 μm to 250 μm to 500 μm (i.e., ranging between any two of the preceding values). In certain beneficial embodiments, the microparticles may range from 50 μm to 150 μm in width.

In certain beneficial embodiments, the microparticles may comprise a bioerodible core and at least two different bioerodible layers over the core. The bioerodible core comprises the second drug. The bioerodible core may also comprise additional optional ingredients such as one or more bioerodible polymers and/or one or more optional supplemental agents. The bioerodible core may be surrounded by a first bioerodible layer that comprises one or more bioerodible polymers and substantially no drug (i.e., less than 5% drug, more typically, less than 1% drug, even more typically, no drug, except for possible impurity amounts of a drug). The first bioerodible layer may also comprise one or more optional supplemental agents. The first bioerodible layer may, in turn, be surrounded by a second bioerodible layer that comprises the first drug. The second bioerodible layer may also comprise additional optional ingredients such as one or more bioerodible polymers and/or one or more optional supplemental agents.

One particular embodiment is illustrated in FIG. 1, which shows a microparticle 100 comprising (a) a bioerodible core that comprises microparticles of the second drug 110 in a bioerodible polymer matrix 112, (b) a first bioerodible layer 114 comprising one or more bioerodible polymers, and (c) a second bioerodible layer that comprises the first drug 116 in a bioerodible polymer matrix 118.

In certain embodiments, the microparticles may further comprise a first additional bioerodible layer that that surrounds the second bioerodible layer and comprises one or more bioerodible polymers and substantially no drug (i.e., less than 5% drug, more typically, less than 1% drug, even more typically no drug, except for possible impurity amounts). The first additional bioerodible layer may also comprise one or more optional supplemental agents. The first additional bioerodible layer may, in turn, be surrounded by a second additional bioerodible layer that comprises an additional drug, which may be the same as or different from the first and second drugs. The second additional bioerodible layer may also comprise additional optional ingredients such as one or more bioerodible polymers and/or one or more optional supplemental agents. In these embodiments, the second additional bioerodible layer will result in initial release of the additional drug, followed by a period of delay (lag period) as the first additional bioerodible layer (which contains substantially no drug) bioerodes, after which the second bioerodible layer bioerodes and releases the first drug, followed by a second period of delay (lag period) as the first bioerodible layer (which contains substantially no drug) bioerodes, after which the core bioerodes and releases the second drug. Additional layers may be added to release additional drugs in the same fashion.

In some embodiments, at least two different types of microparticles may be produced. In one specific example, first and second microparticles are provided. The first microparticles comprise the first drug and are configured for immediate drug release. The first microparticles may also comprise additional optional ingredients such as one or more bioerodible polymers and/or one or more optional supplemental agents. The second microparticles comprise the second drug and are configured for delayed release. The second microparticles may comprise a bioerodible core that comprises the second drug surrounded by a bioerodible layer which contains substantially no drug, but which allows for a delay in time (lag period) before releasing the second drug. The bioerodible core may also comprise additional optional ingredients such as one or more bioerodible polymers and/or one or more optional supplemental agents. The bioerodible layer may comprise one or more bioerodible polymers, one or more optional supplemental agents, and substantially no drug (i.e., less than 5% drug, more typically, less than 1% drug, even more typically no drug, except for possible impurity amounts).

In certain embodiments, additional microparticles may be provided along with the first and second microparticles. The additional microparticles may comprise an additional drug (which may be the same as or different from the first and second drugs) and may be configured for release that is delayed for a greater period than the delayed release of the second microparticles, thereby allowing for drug release in three stages. The additional microparticles may comprise a bioerodible core that comprises the additional drug surrounded by a bioerodible layer which contains substantially no drug, but which allows for a delay in time before releasing the additional drug. The bioerodible core may also comprise additional optional ingredients such as one or more bioerodible polymers and/or one or more optional supplemental agents. The bioerodible layer may comprise one or more bioerodible polymers, one or more optional supplemental agents, and substantially no drug (i.e., less than 5% drug, more typically, less than 1% drug, even more typically no drug, except for possible impurity amounts).

Bioerodible polymers for forming microparticles in accordance with the present disclosure may be selected from suitable members of the following, among many others: (a) polyester homopolymers and copolymers such as polyglycolide, poly-L-lactide, poly-D-lactide, poly-D,L-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-glycolide) (PLGA), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], and poly(sebacic acid-co-fumaric acid), among others, (b) poly(ortho ester) homopolymers and copolymers such as those synthesized by copolymerization of various diketene acetals and diols, among others, (c) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others, (d) polyether homopolymers and copolymers including polyethylene oxide, polybutylene oxide, and poly(ethylene oxide-co-butylene oxide), among others, and (e) amino-acid-based homopolymers and copolymers including tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyester-amides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, among others.

In some embodiment, polymer degradation rates may be tailored based on modification of the ratio of two polymers within a polymer blend and/or modification of monomer ratio within a selected copolymer (e.g., selected from those above, among others), among other strategies.

Examples of supplemental agents, include, for example, imaging agents, among other possibilities. Beneficial imaging agents include (a) contrast agents for use in connection with x-ray fluoroscopy, including metals (e.g., tungsten, platinum, gold, and others), metal salts and oxides (particularly bismuth and barium salts and oxides), and iodinated compounds, among others, (b) contrast agents for use in conjunction with ultrasound imaging, including inorganic and organic echogenic particles (i.e., particles that result in an increase in the reflected ultrasonic energy) or inorganic and organic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid.

Microparticles, with or without surrounding/encapsulating bioerodible layers, may be formed by various methods, including spray drying, pan coating, air suspension coating, ink jet printing, 3D printing, or roll coating.

The microparticles may be introduced into the vasculature of the patient by various routes including via a microcatheter via an endoscope with a distal spray nozzle, or via a balloon delivery system, using conventional arterial and venous access sites, depending on the flow of blood direction.

As previously noted, in a traditional TACE procedure, a patient may have to undergo multiple interventions, which can cause stress and be physically demanding on the patient. The microparticles described herein, however, reduce the number of interventions required by allowing for a first chemotherapy treatment based on the first drug, followed by a lag period (which can, inter alia, allow the patient to rest between exposures to chemotherapy), followed by a second chemotherapy treatment based on the second drug. In some embodiments, one or more additional rest periods are provided, followed by release of one or more additional drugs.

Figure 2A:
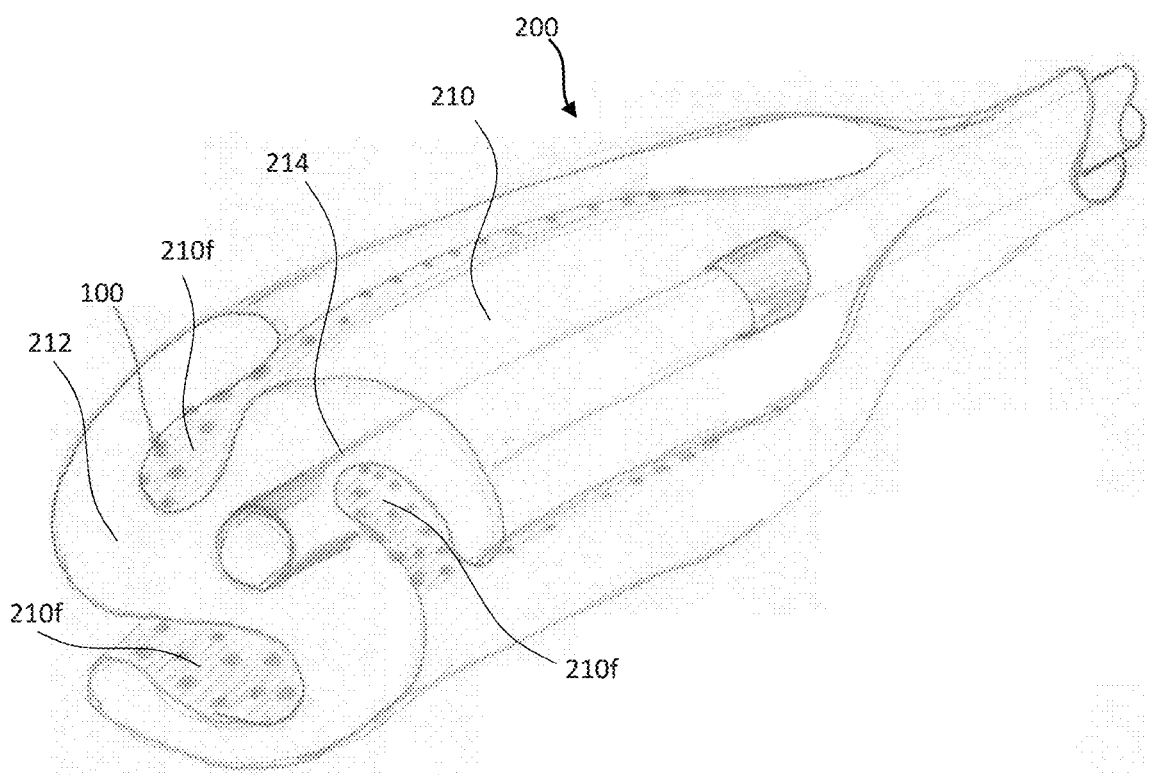
FIG. 2A is a schematic, partially transparent, perspective view of a chemotherapeutic delivery balloon while in a deflated state.
Figure 2B:
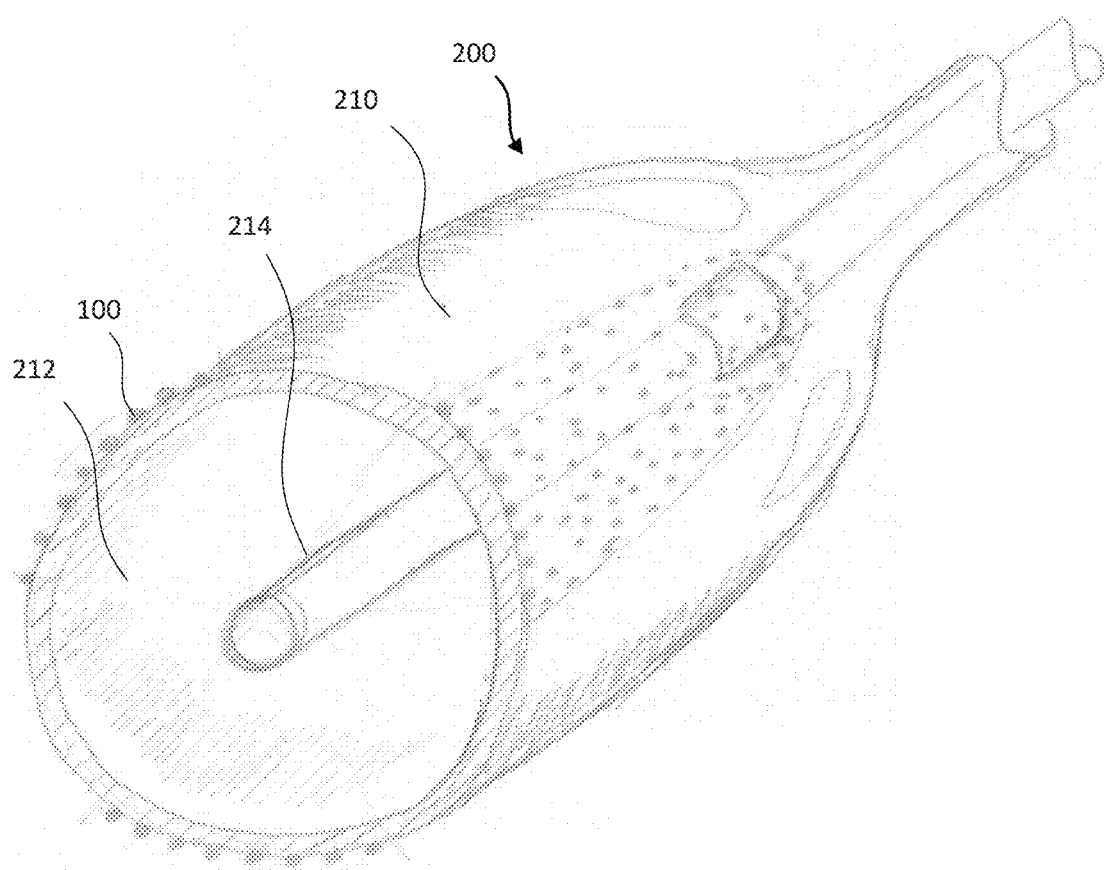
FIG. 2B is a schematic, partially transparent, perspective view of a chemotherapeutic delivery balloon while in an inflated state.

With regard to catheter delivery, and with reference to FIGS. 2A-2B, in some embodiments, a balloon catheter 200 may be used to deliver the microparticles 100. The balloon catheter 200 may comprise an inner tubular member 214 (which allows the balloon catheter 200 to be advanced over a guidewire, not shown) and a balloon 210. A lumen 212 is formed between the balloon 210 and the inner tubular member 214. When in a deflated state, the balloon 210 may be provided with one or more folds 210f, by which the balloon 210 may be wrapped around the tubular member 214. Although three folds (more specifically, three concave folds 210f, with respect to the outer surface of the balloon) are shown in FIGS. 2A-2B, the balloon 210 may have one, two, four, five, six, seven, eight, or more folds. Microparticles 100 as described hereinabove may be loaded on the balloon 210 in regions that are located within the folds 210f. In this way, the microparticles 100 may be protected on the inside of the folds 210f of the balloon 210 during delivery, while still remaining of an outer surface of the material forming the balloon 210. This prevents the microparticles 100 from being flushed away during delivery. Upon inflation, the folds will disappear with the result being that the microparticles 100 are made available for delivery on the surface of the balloon 210 as shown in FIG. 2B. The microparticles 100 may be positioned on the surface of the balloon 210 prior to folding by any suitable process, for example, the microparticles may be adhered to the surface of the balloon by ink jet printing, 3D printing, roll coating or another suitable process.

Alternatively, the microparticles may be positioned into the pre-established balloon folds using any suitable process, for example, via injection into the folds using a microsyringe, or by another suitable technique, after the balloon is formed and folded.

In certain embodiments, a balloon catheter in accordance with present disclosure may be suitably dimensioned for drug release of microparticles in a hepatic artery.

Suitable materials for forming the balloon, include, for example, polyether block amide (e.g., PEBAX), polyethylene terephthalate, nylon, and polyurethane, among others.

Certain embodiments of the present disclosure have been described above. It is, however, expressly noted that the present disclosure is not limited to those embodiments, but rather the intention is that additions and modifications to what was expressly described herein are also included within the scope of the disclosure. Moreover, it is to be understood that the features of the various embodiments described herein were not mutually exclusive and can exist in various combinations and permutations, even if such combinations or permutations were not made express herein, without departing from the spirit and scope of the disclosure. In fact, variations, modifications, and other implementations of what was described herein will occur to those of ordinary skill in the art without departing from the spirit and the scope of the disclosure. As such, the disclosure is not to be defined only by the preceding illustrative description.

What is claimed is:

1. A delivery system comprising:
   a delivery device configured to release microparticles into a feeder artery within a body of a subject, and
   microparticles that are configured to release a first drug over a first time period and to release a second drug over a second time period,
      wherein a lag period of substantially no drug release occurs between the first and second time periods, and wherein the first drug and the second drug may be the same or different,
      wherein the lag period ranges from 2 to 6 weeks, and wherein the first time period is a period of five days or less,
      wherein the second time is a period of five days or less, and
      wherein the microparticles comprise first microparticles that comprise the first drug but not the second drug which are configured for immediate release of the first drug over the first time period and second microparticles that comprise the second drug but not the first drug which configured for delayed release of the second drug over the second time period, the second microparticles comprising a bioerodible core that comprises the second drug surrounded by a first bioerodible layer which contains substantially no drug.

2. The delivery system of claim 1, wherein the first and second drugs are anticancer drugs.

3. The delivery system of claim 1, wherein the first and second drugs are the same.

4. The delivery system of claim 1, wherein the second microparticles further comprise a second bioerodible layer surrounding the first bioerodible layer that comprises the first drug.

5. The delivery system of claim 4, wherein the bioerodible core, the first bioerodible layer and the second bioerodible layer each comprises a polyester homopolymer or copolymer.

6. The delivery system of claim 5, wherein the first and second drugs are the same and are doxorubicin.

7. The delivery system of claim 5, wherein 30 to 70% of the total cumulative drug release from the microparticles occurs over the first time period, wherein 30 to 70% of the total cumulative drug release from the microparticles occurs over the second time period, and wherein less than 5% of the total cumulative drug release occurs over the lag period.

8. The delivery system of claim 1, wherein the delivery device comprises a balloon.

9. The delivery system of claim 8, wherein the microparticles are provided on a surface of the balloon.

10. The delivery system of claim 8, wherein the balloon comprises folds and the microparticles are positioned within the folds.

11. The delivery system of claim 1, wherein 30 to 70% of the total cumulative drug release from the microparticles occurs over the first time period, wherein 30 to 70% of the total cumulative drug release from the microparticles occurs over the second time period, and wherein less than 5% of the total cumulative drug release occurs over the lag period.

12. A method of treatment comprising delivering therapeutic-agent releasing microparticles in accordance with claim 1 into a feeder artery of a tumor with the delivery device of claim 1, wherein the microparticles release the first drug over the first time period, wherein the microparticles release the second drug over the second time period, wherein the lag period of substantially no drug release occurs between the first and second time periods, and wherein the first drug and the second drug are anticancer drugs that may be the same or different.

13. The method of claim 12, wherein the first and second drugs are the same.

14. The method of claim 12, wherein 30 to 70% of the total cumulative drug release from the microparticles occurs over the first time period, wherein 30 to 70% of the total cumulative drug release from the microparticles occurs over the second time period, and wherein less than 5% of the total cumulative drug release occurs over the lag period.

15. The method of claim 12, wherein the second microparticles further comprise a second bioerodible layer surrounding the first bioerodible layer that comprises the first drug.

16. The method of claim 12, wherein the microparticles are released into the artery from a balloon.

17. The method of claim 16, wherein the balloon comprises folds and the microparticles are positioned within the folds in order to be delivered to the artery, wherein the balloon is inflated thereby releasing the microparticles from the folds into the artery.

18. A delivery system comprising:
a delivery device configured to release microparticles into a feeder artery within a body of a subject, and
microparticles that are configured to release a first drug over a first time period and to release a second drug over a second time period,
wherein a lag period of substantially no drug release occurs between the first and second time periods, and wherein the first drug and the second drug may be the same or different,
wherein the lag period ranges from 2 to 6 weeks, and wherein the first time period is a period of five days or less,
wherein the second time is a period of five days or less, and
wherein the delivery device comprises a balloon.

19. The delivery system of claim 18, wherein the first and second drugs are anticancer drugs.

20. The delivery system of claim 18, wherein the first and second drugs are the same.

21. The delivery system of claim 18, wherein the microparticles comprise a bioerodible core that comprises the second drug, a first bioerodible layer surrounding the bioerodible core that comprises substantially no drug, and a second bioerodible layer surrounding the first bioerodible layer that comprises the first drug.

22. The delivery system of claim 21, wherein the bioerodible core, the first bioerodible layer and the second bioerodible layer each comprises a polyester homopolymer or copolymer.

23. The delivery system of claim 22, wherein the first and second drugs are the same and are doxorubicin.

24. The delivery system of claim 22, wherein 30 to 70% of the total cumulative drug release from the microparticles occurs over the first time period, wherein 30 to 70% of the total cumulative drug release from the microparticles occurs over the second time period, and wherein less than 5% of the total cumulative drug release occurs over the lag period.

25. The delivery system of claim 18, wherein the microparticles are provided on a surface of the balloon.

26. The delivery system of claim 18, wherein the balloon comprises folds and the microparticles are positioned within the folds.

27. The delivery system of claim 18, wherein the microparticles comprise first microparticles that comprise the first drug but not the second drug which are configured for immediate release of the first drug over the first time period and second microparticles that comprise the second drug but not the first drug which configured for delayed release of the second drug over the second time period, the second microparticles comprising a bioerodible core that comprises the second drug surrounded by a bioerodible layer which contains substantially no drug.

28. The delivery system of claim 18, wherein 30 to 70% of the total cumulative drug release from the microparticles occurs over the first time period, wherein 30 to 70% of the total cumulative drug release from the microparticles occurs over the second time period, and wherein less than 5% of the total cumulative drug release occurs over the lag period.

29. A method of treatment comprising delivering therapeutic-agent releasing microparticles in accordance with claim 18 into a feeder artery of a tumor with the delivery device of claim 18, wherein the microparticles release the first drug over the first time period, wherein the microparticles release the second drug over the second time period, wherein the lag period of substantially no drug release occurs between the first and second time periods, and wherein the first drug and the second drug are anticancer drugs that may be the same or different, wherein the microparticles are released into the artery from the balloon.

30. The method of claim 29, wherein the first and second drugs are the same.

31. The method of claim 29, wherein 30 to 70% of the total cumulative drug release from the microparticles occurs over the first time period, wherein 30 to 70% of the total cumulative drug release from the microparticles occurs over the second time period, and wherein less than 5% of the total cumulative drug release occurs over the lag period.

32. The method of claim 29, wherein the microparticles comprise a bioerodible core that comprises the second drug, a first bioerodible layer surrounding the bioerodible core that comprises substantially no drug, and a second bioerodible layer surrounding the first bioerodible layer that comprises the first drug, or wherein the microparticles comprise first microparticles that comprise the first drug but not the second drug and release the first drug over the first time period and second microparticles that comprise the second drug but not the first drug and release the second drug over the second time period.

33. The method of claim 29, wherein the balloon comprises folds and the microparticles are positioned within the folds in order to be delivered to the artery, wherein the balloon is inflated thereby releasing the microparticles from the folds into the artery.

* * * * *